(12) United States Patent
Ebel et al.

(10) Patent No.: US 8,648,031 B2
(45) Date of Patent: Feb. 11, 2014

(54) MACROCYCLIC LACTONES

(75) Inventors: Klaus Ebel, Lampertheim (DE); Bernhard Brunner, Heidelberg (DE); Christoph Stock, Ellerstadt (DE); Ralf Pelzer, Fürstenberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/537,823

(22) Filed: Jun. 29, 2012

(65) Prior Publication Data

US 2013/0005641 A1    Jan. 3, 2013

Related U.S. Application Data

(60) Provisional application No. 61/502,883, filed on Jun. 30, 2011.

(51) Int. Cl.
*A61Q 13/00* (2006.01)

(52) U.S. Cl.
USPC ............................................. 512/11

(58) Field of Classification Search
USPC ............................................. 512/11
See application file for complete search history.

(56) References Cited

U.S. PATENT DOCUMENTS

| | | | |
|---|---|---|---|
| 3,856,815 A | 12/1974 | Hopp et al. | |
| 3,890,353 A | 6/1975 | Becker | |
| 4,056,541 A | 11/1977 | Hoffman et al. | |
| 4,268,445 A | 5/1981 | Kropp et al. | |
| 5,266,559 A | 11/1993 | Fankhauser et al. | |
| 5,936,100 A * | 8/1999 | Furstner et al. | 549/266 |
| 6,008,185 A | 12/1999 | Bertram et al. | |
| 8,410,293 B2 | 4/2013 | Ebel et al. | |

FOREIGN PATENT DOCUMENTS

| | | |
|---|---|---|
| DE | 2136496 A1 | 2/1973 |
| DE | 2511410 A1 | 9/1976 |
| DE | 2906296 A1 | 8/1980 |
| DE | 29 16 418 A1 | 11/1980 |
| DE | 2916418 A1 | 11/1980 |
| EP | 0862911 A2 | 9/1998 |
| GB | 1266092 A | 3/1972 |
| JP | 201095447 A | 4/2010 |
| JP | 2010095447 A | 4/2010 |
| WO | WO-2008066299 A1 | 6/2008 |
| WO | WO-2008133441 A1 | 11/2008 |

OTHER PUBLICATIONS

Fukawa, Toyotama Koryo KK, 201, pp. 6-7.
Chemical Abstracts Service, Columbus, Ohio US XP002663487.
U.S. Appl. No. 61/502,879.
Chemical Abstracts Service, XP002663487, Dec. 20, 2007, Database Accession No. 959046-58-3.
Bonifazi, Evelyn L., et al., "Antiproliferative Activity of Synthetic Naphthoquinones Related to Lapachol. First Synthesis of 5-Hyrdoxylapachol", Bioorganic & Medicinal Chemistry, vol. 18, (2010), pp. 2621-2630.
Danet, Michele, et al., "Enantioselective Synthesis of the Originally Proposed Usneoidone Structure: Evidence for a Structural Revision", Eur. J. Org. Chem., (2004), pp. 1911-1922.
Schreiber, J. Am. Chem. Soc., 102, 1980, p. 6163.
Thomas, Alan F., et al., "Homologues of -Menthane Derivatives in Roman Camomile" Helvetica Chimica Acta, vol. 64, Fasc. 5, No. 136, (1981), pp. 1488-1495.
Zakharkin, L.I., et al., "Syntheses of 2-Oxabicyclo[4.10.0]Hexadec-1(6)-Ene from Cyclododecanone", Russian Chemical Bulletin, vol. 43, No. 4, (1994), pp. 608-611.
U.S. Appl. No. 61/502,879, filed Jun. 30, 2011, Ebel et al.

\* cited by examiner

*Primary Examiner* — Ling Choi
*Assistant Examiner* — Lanee Reuther
(74) *Attorney, Agent, or Firm* — Novak Druce Connolly Bove + Quigg LLP

(57) ABSTRACT

The present invention relates to novel macrocyclic lactones, to processes for their preparation and to their use as fragrances and also to products comprising the novel macrocyclic lactones.

8 Claims, No Drawings

MACROCYCLIC LACTONES

CROSS-REFERENCE TO RELATED APPLICATIONS

This application claims benefit (under 35 USC 119(e)) of U.S. Provisional Application 61/502,883, filed Jun. 30, 2011, which is incorporated by reference.

The present invention relates to novel macrocyclic lactones, to processes for their preparation and to their use as fragrances and also to products comprising the novel macrocyclic lactones.

Cyclic enol ethers are important intermediates in the synthesis of macrocyclic lactones, which are used as fragrances. For example, U.S. Pat. No. 3,890,353 describes the preparation of saturated 15-pentadecanolide (Exaltolide®) of the formula (a),

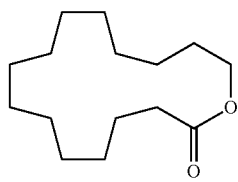

(a)

where the cyclic enol ether 13-oxa-1,12-didehydrobicyclo[10.4.0]hexadecane of the formula (b) serves as starting material.

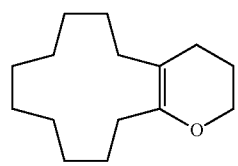

(b)

U.S. Pat. No. 5,266,559 describes that the double-bond isomers of the formula (c) which arise in the synthesis of 15-pentadecanolide and have a double bond either in the 11 or 12 position, in each case in the trans configuration, can preferably be used as musk-like fragrances

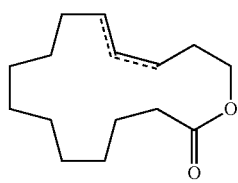

(c)

In addition to the 16-ring lactones described above, 15-ring lactones are also described as musk-like fragrances. For example, EP 0 862 911 describes saturated and unsaturated 15-ring lactones of the formulae (d1) and (d2), where R is methyl or hydrogen.

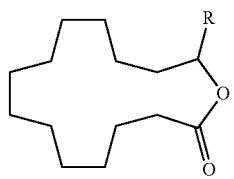

(d1)

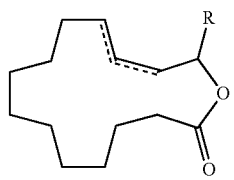

(d2)

The 15-ring lactones can be prepared starting from the corresponding cyclic enol ether of the formula (e).

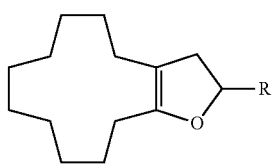

(e)

where R is H or Me

The preparation of cyclic enol ethers, which are suitable as fragrances or for producing fragrances, is described, for example, in GB 1266092, DE 2136496, U.S. Pat. No. 3,890,353, DE 25 11 410, DE 29 06 296 or JP 2010-95447.

The fragrances processing industry is continually looking for new, interesting compounds in order to be able to provide their customers with suitable installations according to their requirements and wishes. In particular, novel compounds which have a musk-like odor are sought as replacements for rare and expensive musk or as scent components for fragrance compositions with musk character.

Proceeding from this prior art, the object was to find novel fragrances.

This object is achieved by compounds of the formulae (I) or (IIa) or mixtures thereof

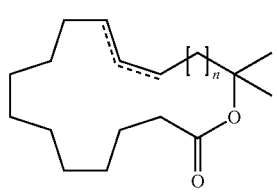

(I)

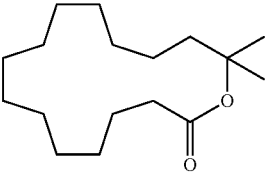

(IIa)

in which
n is zero (0) or one (1) and
the dashed line is an additional double bond in 11 or 12 position in cis or trans configuration.

Here, the term mixtures comprises both mixtures of individual compounds of the formula (I) as well as mixtures of one or more compounds of the formula (I) with the compound (IIa).

In a further embodiment of the invention, the mixture according to the invention furthermore comprises a compound of the general formula (IIb).

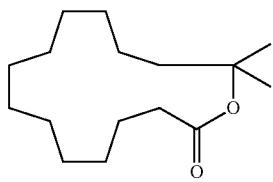
(IIb)

This embodiment of the invention accordingly comprises, for example, mixtures of individual compounds of the formula (I) with the compound of the formula (IIb) as well as mixtures of one or more compounds of the formula (I) with the compound (IIb).

This embodiment of the invention furthermore comprises mixtures of individual compounds of the formula (I) with the compound of the formula (IIa) and the compound of the formula (IIb) as well as mixtures of one or more compounds of the formula (I) with the compound (IIa) and the compound (IIb).

Particular preference is given to compounds of the formula (I) as described above, which are at least one of the double-bond isomers of the formulae (Ia), (Ib), (Ic) or (Id) or mixtures thereof

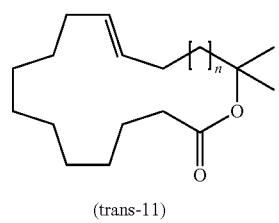
(Ia)
(trans-11)

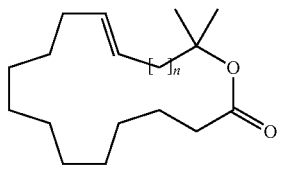
(Ib)
(trans-12)

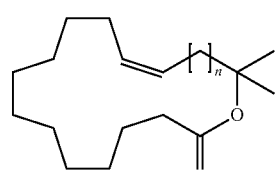
(Ic)
(cis-12)

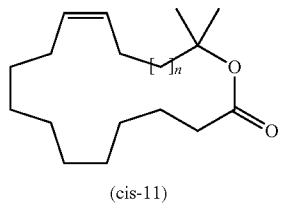
(Id)
(cis-11)

and n is as defined in formula (I).

Particular preference is given to compositions which comprise mixtures of the above-described double-bond isomers of the formulae (Ia), (Ib), (Ic) or (Id), where the mixture has a content of at least 60% by weight, preferably at least 70% by weight, in particular at least 80% by weight up to a maximum of 99.5% by weight, of the compound of the formula (Ia), i.e. the lactone with a trans-configured double bond in position 11 based on the total amount of the compounds of the formulae (I), (IIa) and (IIb) present in the mixture.

Formula (II) comprises the compounds of the formula (IIa) and (IIb):

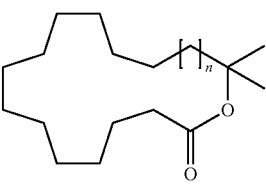
(II)

in which n is zero (0) or one (1)

In the case where n in formula (II) is zero (0), the compound is of the formula (IIb), in the case where n in formula (II) is one (1), the compound is of the formula (IIa).

The compounds of the formulae (I) or (IIa or (IIb) or mixtures thereof, in particular isomer mixtures, comprising at least one of the double-bond isomers of the formulae (Ia), (Ib), (Ic) or (Id) have, compared to the double-bond isomers of the formula (c) described in the introduction, a more intense and overall animalic and rounded odor.

The invention also further provides a process for the preparation of the compounds of the formulae (I) or (IIa) or (IIb) or of the compounds of the formulae (Ia), (Ib), (Ic) or (Id) as described above, comprising the reaction steps:

a) alkylation of the cyclododecanone of the formula (III)

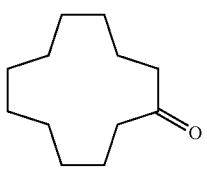
(III)

with a compound of the formula (IVa) or a compound of the formula (IVb)

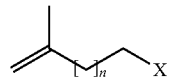
(IVa)

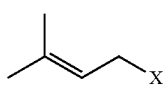
(IVb)

in which, in formula (IVa) and (IVb)
X is a leaving group and
n is zero (0) or one (1),
to give a corresponding compound of the formula (Va) or of the formula (Vb),

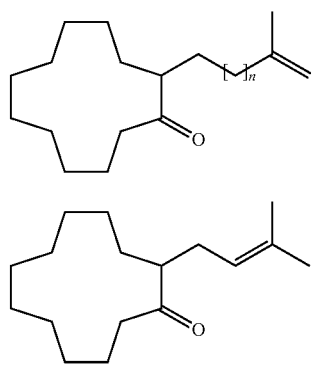

in which, in formula (Va) n is zero (0) or one (1);

b) cyclization of one of the compounds of the formulae (Va) or (Vb) to give a corresponding compound of the formula (VI);

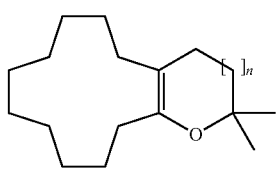
(VI)

in which, in formula (VI), n is zero (0) or one (1);

c) addition of $H_2O_2$ onto the double bond of the compound of the formula (VI) to give a compound of the formula (VII) and subsequent transition metal [TM]—catalyzed fragmentation of the compound of the formula (VII) to give compounds of the formula (I)

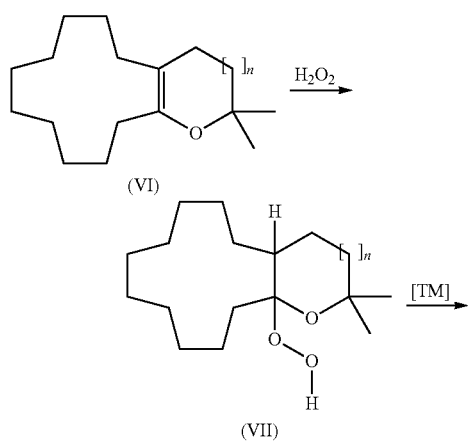

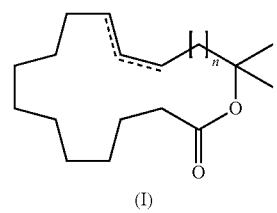
(I)

and optionally d) hydrogenation of the compounds of the formula (I) to give a compound of the formula (II)

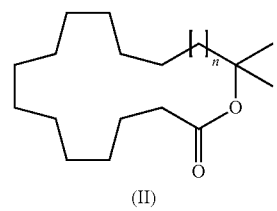

in which, in the formulae (I), (II) and (VII)
n is zero (0) or one (1) and
the dashed line in formula (I) is an additional double bond in 11 or 12 position in cis or trans configuration.

A key step in the process has proven to be process step b), in which, in one preferred embodiment, the cyclization was carried out in the presence of a Brönsted acid or Lewis acid as reactive distillation.

Consequently, the invention also further provides a process for the preparation of the compounds of the formulae (I) or (IIa) or (IIb) or of the compounds of the formulae (Ia), (Ib), (Ic) or (Id) as described above, comprising, as one of the reaction steps, a cyclization of a compound of the formula (Va) or of the formula (Vb),

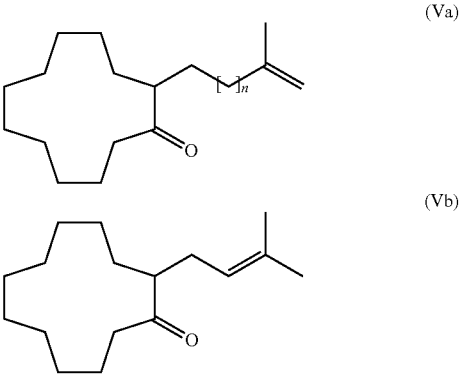

to give a corresponding compound of the formula (VI);

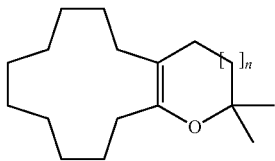

(VI)

in which, in formulae (Va) and (VI), n is zero (0) or one (1), wherein the cyclization is carried out in the presence of a Brönsted acid or Lewis acid as reactive distillation, where the compound of the formula (VI) formed is separated off from the compound of the formula (Va) or of the formula (Vb) by distillation from the reaction mixture.

In process step a) of the process according to the invention, cyclododecanone (CDon) of the formula (III), an industrially produced intermediate,

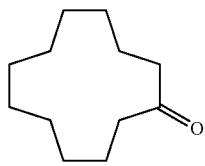

(III)

is alkylated with a compound of the formula (IVa) or a compound of the formula (IVb)

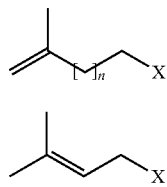

(IVa)

(IVb)

in which, in formula (IVa) and (IVb)
 X is a leaving group and
 n is zero (0) or one (1), preferably zero (0),
to give a corresponding compound of the formula (Va) or of the formula (Vb),

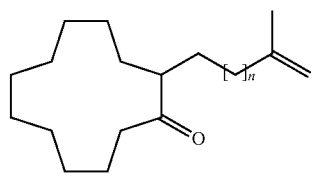

(Va)

(Vb)

in which, in formula (Va), n is zero (0) or one (1), preferably zero (0).

The leaving group X is functional groups known to the person skilled in the art as are customarily used in nucleophilic substitution reactions. Nonlimiting examples of X are Cl, Br, I, $OSO_2C_6H_4Me$, $OSO_2Me$, $OSO_2CF_3$, $OSO_2C_4F_9Me$, $OSO_2C_6H_4Me$, $OSO_2C_6H_4Me$. Preferably, X is Cl or Br, in particular Cl.

The monoalkylation of cyclododecanone (CDon) can be carried out by processes known to the person skilled in the art. For example, CDon can be reacted firstly with chloroformic acid alkyl ester to give the corresponding beta-ketocarboxylic acid ester which, following alkylation with a compound of the formula (IVa) or a compound of the formula (IVb), subsequent saponification and decarboxylation depending on the alkylating reagent used, is converted to a compound of the formula (Va) or (Vb), as is described in principle for example in GB 1266092.

Preferably, the monoalkylation of cyclododecanone (CDon) is carried out by direct reaction of CDon with an alkylating agent of the formula (IVa) or of the formula (IVb) in the presence of a base and a phase transfer catalyst (PTC), as described for example in DE 2916418. The PTC used are preferably low-cost tetraalkylammonium halides, for example tetrabutylammonium iodide, and the base used is low-cost alkali metal or alkaline earth metal hydroxide, in particular sodium hydroxide.

In process step b) of the process according to the invention, a compound of the formula (Va) or of the formula (Vb) is cyclized to give a corresponding compound of the formula (VI)

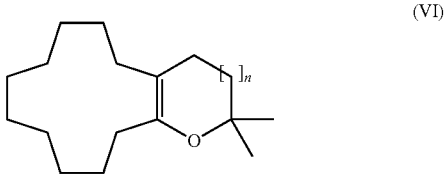

(VI)

in which, in formula (VI), n is zero (0) or one (1). The compound of the formula (Vb) is cyclized to give a compound of the formula (VI) where n is 1.

Preferably, the cyclization takes place in the presence of a Brönsted acid or Lewis acid, preferably a Brönsted acid, where the reaction is carried out as reactive distillation, where the cyclic enol ethers of the formula (VI) formed are separated off from compounds of the formula (Va) or of the formula (Vb) by distillation from the reaction mixture.

The preferred embodiments with regard to process step b) described below also refer to the process described above comprising the cyclization carried out as reactive distillation in the presence of a Brönsted acid or Lewis acid.

In compounds of the formula (Va), n is particularly preferably zero (0), which leads to the formation of the 5-membered cycloenol ether of the formula (VI) where n is zero (0).

The Brönsted acids which can preferably be used in process step b) are either organic or inorganic acids. Preference is given to Brönsted acids which can themselves not react with the compound of the formula (Va) or of the formula (Vb), i.e. are consumed in a reaction, but merely serve as a proton source for a chemical reaction catalyzed by protons. Nonlimiting examples of particularly suitable Brönsted acids are sulfuric acid, phosphoric acid, methanesulfonic acid, acid, p-toluenesulfonic acid, strongly acidic ion exchangers, tetrafluoroboric acid, trifluoroacetic acid, formic acid or oxalic acid.

As Lewis acid, preference is given to using in process step b), for example, aluminum trichloride, tin tetrachloride, titanium tetrachloride, zirconium tetrachloride, iron trichloride or nickel dichloride.

The amount of Brönsted acid or Lewis acid which is preferably used in process step b) can be varied within a wide range. In principle, the molar ratio of the Brönsted acid or Lewis acid to the compound of the formula (Va) or of the formula (Vb) can be greater than, equal to or less than 1. In principle, traces of acids suffice to catalyze the cyclization.

Preferably, in process step b), the molar ratio of the Brönsted acid or Lewis acid, in particular of the Brönsted acid, to the compound of the formula (Va) or of the formula (Vb) is not greater than 1, particularly preferably not greater than 0.15, very particularly preferably between 0.1 and 0.0005, in particular between 0.07 and 0.001.

Preferably, in process step b), the cyclization is carried out in the presence of a Brönsted acid. Preference is given here to using Brönsted acids with a $pK_a$ value of less than 5, particularly preferably less than 2.5, in particular less than 0. The $pK_a$ value of the Brönsted acid is very particularly preferably between −1.5 and −11.

A reactive distillation is a chemical process known in principle to the person skilled in the art, in which a single-stage or multi-stage distillation is combined with a chemical reaction, in the present case a cyclization. The reaction product, in the present case a cyclic enol ether of the formula (VI), is continuously separated off by distillation from the starting material, a ketone.

Preferably, the reactive distillation and/or the cyclization reaction is carried out in a temperature range between 50° C. and 300° C., particularly preferably between 80° C. and 200° C.

Depending on the boiling points of the compounds to be separated, the person skilled in the art can usually ascertain, directly or after a few experiments, suitable measures with regard to the distillation columns which can be used, the required separation efficiency of such a column, and the distillation parameters such as, for example, pressure, temperature and reflux ratio, and/or make a suitable selection in order to be able to carry out process step b) in the desired way.

In process step c) of the process according to the invention, the addition of $H_2O_2$ onto the double bond of the compound of the formula (VI) is carried out to give a compound of the formula (VII) and subsequent transition metal [TM]—catalyzed fragmentation of the compound of the formula (VII) to give compounds of the formula (I),

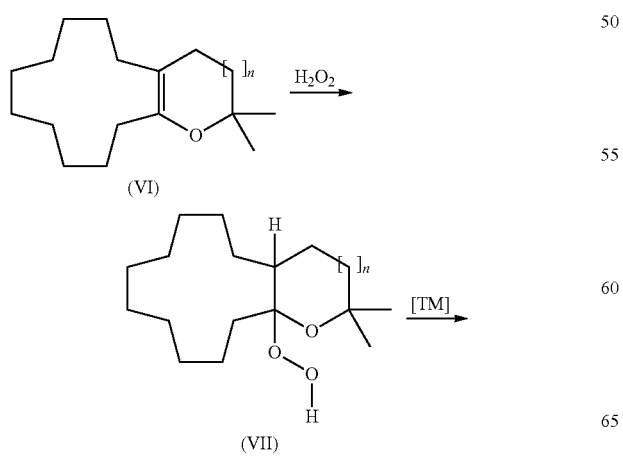

(VI)

(VII)

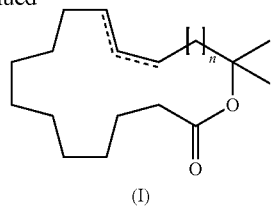

(I)

in which n is zero (0) or one (1) and the dashed line in formula (I) is an additional double bond in 11 or 12 position in cis or trans configuration.

The conditions for the addition of $H_2O_2$ onto the double bond of the compound of the formula (VI) and the subsequent transition-metal-catalyzed fragmentation of the compound of the formula (VII) to give compounds of the formula (I) are known in principle from the literature and are described for example in EP 0 862 911 and the literature cited therein, such as, for example, an article by S. L. Schreiber, J. Am. Chem. Soc. 102 (1980), 6163.

In process step c), the fragmentation of the compound of the formula (VII) to the compound of the formula (I) is carried out particularly preferably in the presence of Cu(II) salts or Fe(II) salts.

The compounds of the formula (I) formed in process step c) are in particular the double-bond isomers of the formulae (Ia), (Ib), (Ic) or (Id) or mixtures thereof.

(Ia)

(trans-11)

(Ib)

(trans-12)

(Ic)

(cis-12)

(Id)

(cis-11)

Preferably, in process step c), predominantly the trans-configured double-bond isomers of the formulae (Ia) and (Ib) are formed. In addition, the formation of small amounts of the saturated compounds of the formula (II) are observed. The molar ratio of the trans-configured double-bond isomers of the formulae (Ia) and (Ib) to the cis-configured double-bond isomers of the formulae (Ic) and (Id) is preferably greater than 2, particularly preferably greater than 3, in particular greater than 4. In process step c), in particular the trans-configured double-bond isomer of the formula (Ia) is formed, i.e. the lactone in which the double bond is in position 11.

The optional process step d) is the hydrogenation of the compounds of the formula (I) to give a compound of the formula (II),

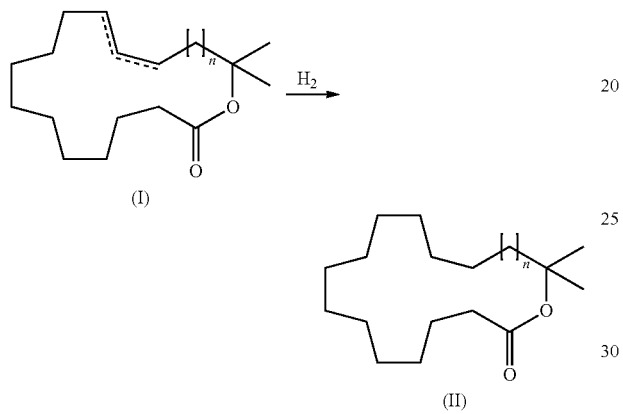

in which n is zero (0) or one (1) and the dashed line in formula (I) is an additional double bond in 11 or 12 position in cis or trans configuration.

Preferably, in process step d), the hydrogenation is carried out with hydrogen in the presence of a transition metal catalyst.

The transition metal catalyst and reaction conditions which can be used for the hydrogenation of the double bond in the compounds of the formula (I) are known in principle to the person skilled in the art. U.S. Pat. No. 3,890,353 describes, for example, the hydrogenation of 15-pentadec-(11 and 12)-enolid in the presence of Raney nickel.

The compounds of the formulae (I) and/or (IIa) and/or (IIb) according to the invention or the compounds of the formulae (Ia), (Ib), (Ic) and/or (Id) have, as described previously, a musk-like odor.

The present invention also further provides the use of the compounds of the formulae (I) and/or (IIa) and/or (IIb) or of the compounds of the formulae (Ia), (Ib), (Ic) and/or (Id) as described above as fragrances.

The compounds of the formulae (I) and/or (IIa) and/or (IIb) according to the invention or the compounds of the formulae (Ia), (Ib), (Ic) and/or (Id) as described above can be used not only by themselves as fragrance, but are preferably used in combination with known fragrances, as are described, for example, in K. Bauer, D. Garbe and H. Surburg, Common Fragrance and Flavor Materials, 4th Edition, Wiley-VCH, Weinheim 2001.

The present invention therefore also further provides the use of the compounds of the formulae (I) and/or (IIa) and/or (IIb) or of the compounds of the formulae (Ia), (Ib), (Ic) and/or (Id) as described above as fragrance together with at least one further fragrance in a fragrance composition.

The present invention likewise provides fragrance compositions comprising at least one of the compounds of the formulae (I) and/or (IIa) and/or (IIb) or of the compounds of the formulae (Ia), (Ib), (Ic) and/or (Id) as described above together with at least one further fragrance.

As further fragrance, preference is given to using the fragrances which have a musk-like odor, a citrus note, a woody note, an oriental note or a leather note.

The compounds of the formulae (I) and/or (IIa) and/or (IIb) according to the invention or the compounds of the formulae (Ia), (Ib), (Ic) and/or (Id) as described above can on the one hand be used in fine perfumery, but on the other hand they can also be used for the perfuming of various products or articles, such as, for example, for the perfuming of cosmetics such as creams, lotions, aerosols, toilet soap, technical articles, detergents, fabric softeners, disinfectants or textile treatment compositions.

The present invention therefore also provides a perfumed or aromatized product or article comprising organoleptically active amounts of at least one of the compounds of the formulae (I) and/or (IIa) and/or (IIb) or of the compounds of the formulae (Ia), (Ib), (Ic) and/or (Id) as described above.

The invention is explained by the following examples although these do not limit the invention.

Example 1

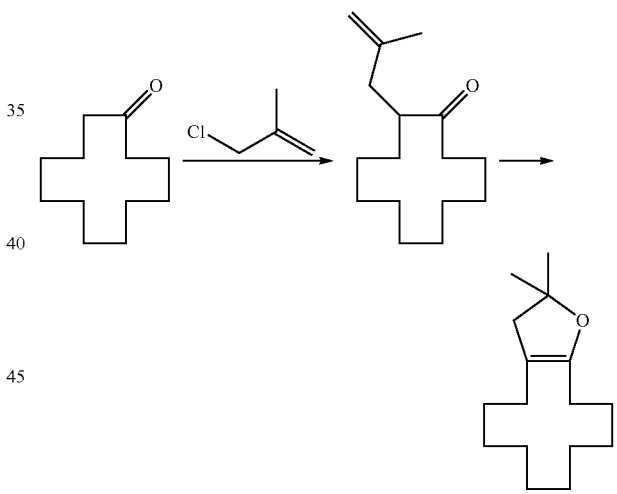

Allylation:

CDon (364.6 g), toluene (360 ml), tetrabutylammonium iodide (7.6 g) and sodium hydroxide solution (50% strength, 480 g) were introduced into the reactor and heated to 90° C. with stirring (400 rpm). At an internal temperature of 90° C., the metered addition of methallyl chloride (362.2 g) was started, during which the temperature in the reactor dropped and reflux started. Overall metering time: 3 h. The two-phase reaction mixture was then stirred overnight at 94° C. The reaction solution was then cooled to RT. At 65° C., 500 ml of water were added in order to dissolve the accumulated solid in the aqueous phase. Following phase separation, the organic phase was washed twice with 500 ml of water. The organic phase was then also washed with 500 g of 10% strength sulfuric acid. The aqueous phases were discarded in each case.

Cyclization:

Brönsted Acid Catalysis 1006 g of methallylcyclododecane were introduced as initial charge in a 1000 ml three-neck flask with 30 cm Sulzer column and Normag column head and admixed with 20 g of concentrated sulfuric acid. A vacuum of 1 mbar was applied, and the oil-bath temperature was increased to 140° C. At a bottom temperature of 128-135° C., the bicycle was slowly distilled out of the reaction mixture (overhead temperature 91-96° C.). In total, 866.35 g of product could be distilled out of the reaction mixture.

Lewis Acid Catalysis 200 g of 2-(2-methallyl)cyclododecanone were introduced as initial charge in a 500 ml distillation flask with 30 cm packed column (3 mm wire rings) and Normag column head and admixed with 2 g aluminum chloride. A vacuum of 2 mbar was applied, and the oil-bath temperature was slowly increased to 175° C. At a bottom temperature of 153-156° C., the product was distilled out of the reaction mixture (overhead temperature 121-123° C.). In total, 140.5 g of product could be distilled out of the reaction mixture.

Example 2

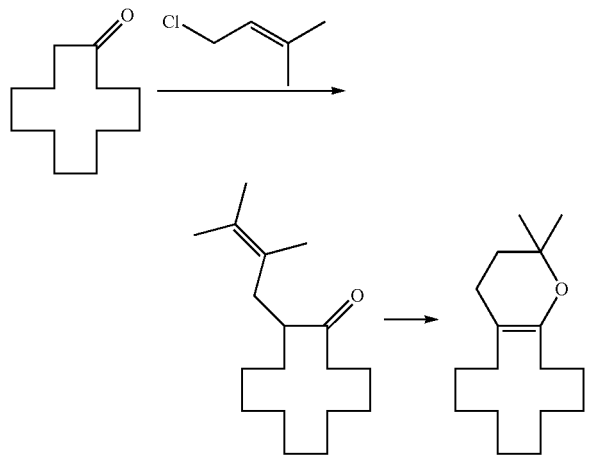

CDon (364.6 g), toluene (360 ml), tetrabutylammonium iodide (7.6 g) and sodium hydroxide solution (50% strength, 480 g) were introduced into the reactor and heated to 90° C. with stirring (400 rpm). At an internal temperature of 90° C., the metered addition of 1-chloro-3-methyl-2-butene (313.7 g) was started. The temperature was held at 90° C. throughout the entire addition. Overall metering time: 3 h. The two-phase reaction mixture was after-stirred for 5 h at 90° C. The reaction solution was then cooled to RT. At 65° C., 500 ml of water were added in order to dissolve the accumulated solid in the aqueous phase. Following phase separation, the organic phase was washed twice with 500 ml of water. The organic phase was then also washed with 500 g of 10% strength sulfuric acid. The aqueous phases were discarded in each case.

7 g of conc. sulfuric acid were added to 278 g of the intermediate and then the solution was transferred to a 1 l distillation flask and distilled in a 70 cm packed column (3 mm metal Raschig rings) with reflux divider at a bottom temperature of 185° C., an overhead temperature of 130-135° C., a pressure of 3 mbar and a reflux ratio of from 40:1 to 60:1. 191.7 g of the product could be distilled out of the reaction mixture.

Example 3

Preparation of 14-Dimethyltetradecenolid a) Hydroperoxide Formation 764 g of 14-dimethyl-13-oxabicyclo[10.3.0]pentadec-[1(12)]-ene (3.2 mol) from Example 1 were introduced as initial charge together with 1900 g of propionic acid and 8.0 g of concentrated $H_2SO_4$ in a 1 liter three-neck flask and cooled to 0° C. 295 g of a 50% strength $H_2O_2$ solution were then slowly added dropwise over the course of 45 minutes. The reaction mixture was after-stirred for 2 hours at 0-5° C., during which a white suspension was formed. The sulfuric acid was then neutralized by adding 63 g of a 10% strength NaOH solution.

b) Fragmentation 300 g of polyethylene glycol 400 (available commercially as Lutrol® E400) were introduced as initial charge together with 4.7 g of $Cu(OAc)_2$ in a 1 liter distillation apparatus. The mixture was heated to 100-110° C. at a pressure of 20 mbar. Using a wobble-head pump, the cooled hydroperoxide solution from a) was metered into the PEG solution over the course of 2-3 hours. In parallel to this, an azeotrope of propionic acid and water was continuously distilled off from the reaction solution. The reaction product obtained in this way was distilled firstly over a simple bridge at 5 mbar and at a bottom temperature of 140° C. The distillate from the rough distillation was then subjected to fine distillation over a 20 cm packed column at a pressure of 0.5-1 mbar and a transition temperature of 85-99° C. In this way, 540 g of a 14-dimethyltetradecenolid mixture with a purity of >95% were obtained. The isomer distribution of the 14-dimethyltetradecenolid mixture was determined by means of NMR spectroscopy, GC-MS and GC-IR as 82% trans-14-dimethyltetradec-11-en-14-olid (retention time: 28.31 minutes)

2% trans-14-dimethyltetradec-12-en-14-olid (retention time: 27.35 minutes)

11% cis-14-dimethyltetradec-11-en-14-olid (retention time: 28.49 minutes)

2% cis-14-dimethyltetradec-12-en-14-olid (retention time: 27.30 minutes)

3% dimethyltetradecan-14-olid (retention time: 27.61 minutes).

GC-MS: 30 m column DB-WAX ID: 0.32 mm FD: 0.25 μm; temperature program: 50° C. at 5° C. per minute to 240° C. and 25 minutes isotherm.

NMR ($^{13}C$, 150 MHz, $C_6D_6$) δ (ppm): 172.4 (s, cis+trans), 133.6 (d, trans), 132.5 (d, cis), 126.2 (d, trans), 124.8 (d, cis), 81.1 (s, trans), 80.8 (s, cis), 43.6 (t, trans), 38.5 (t, cis), 35.0 (t, cis), 34.8 (t, trans), 30.9 (t, trans), 28.1 (t, cis), 27.7 (t, trans), 27.5 (t, trans), 27.3 (t, trans), 26.8 (t, cis), 26.6 (q, cis), 26.57 (t, cis), 26.4 (q, trans), 26.3 (t, trans), 26.2 (t, trans), 26.15 (t, cis), 26.1 (t, cis), 25.7 (t, cis), 25.6 (t, cis), 25.5 (t, cis), 25.2 (t, trans), 24.9 (t, trans), 23.7.

NMR (1H, 600 MHz, $C_6D_6$) δ (ppm) trans-14-dimethyltetradecen-11-olid: 4.40-5.52 (1H, dt, $J_1$=15.6 Hz, $J_2$=6.95 Hz); 5.3-5.4 (1H, dt, $J_1$=15.6 Hz, $J_2$=6.7 Hz); 2.47 (2H, d); 2.15 (2H, t), 2.05 (2H, m), 1.2-1.6 (m, 12H), 1.41 (6H, s).

Example 4

Procedure for the Preparation of 15-Dimethylpentadecenolid a) Hydroperoxide Formation 50 g of 14-dimethyl-13-oxabicyclo[10.4.0]-hexadec-[1(12)]-ene from example 2 are introduced as initial charge together with 115 g of propionic acid and 0.6 g of concentrated $H_2SO_4$ in a 1 liter three-neck flask and cooled to 0° C. 17.8 g of a 50% strength $H_2O_2$ solution are then slowly added dropwise over the course of 45 minutes. The reaction mixture is after-stirred for 2 hours at 0-5° C., during which a white suspension should be formed. The sulfuric acid is then neutralized by adding 5 g of a 10% strength NaOH solution.

b) Fragmentation 100 g of polyethylene glycol 400 (commercially available as Lutrol® E400) are introduced as initial charge together with 0.3 g of Cu(OAc)$_2$ in a 1 liter distillation apparatus. The mixture is heated to 100-110° C. at a pressure of 20 mbar. Using a wobble-head pump, the cooled hydroperoxide solution from a) is metered into the PEG solution over the course of 2-3 hours. In parallel to this, an azeotrope of propionic acid and water is continuously distilled off from the reaction solution. The reaction product obtained in this way is distilled firstly over a simple bridge at 5 mbar and at a bottom temperature of 150° C. The distillate from the rough distillation is then subjected to fine distillation over a 20 cm packed column at a pressure of 0.5-1 mbar and at a transition temperature of 90-105° C. In this way, 25 g of a 15-dimethylpentadecenolid mixture with a purity of >95% can be obtained.

The 15-dimethylpentadecenolid mixture comprises the double-bond isomers:
trans-15-dimethylpentadec-11-en-15-olid
cis-15-dimethylpentadec-11-en-15-olid
trans-15-dimethylpentadec-12-en-15-olid
cis-15-dimethylpentadec-12-en-15-olid Example 5

Preparation of
14-Dimethyltetradecanolid—Hydrogenation of the
Double Bond 20.6 g of 14-dimethyltetradecenolid from example 3 were introduced as initial charge together with toluene in a 250 ml three-neck flask with a gas burette (1 bar of $H_2$) and heated to 95° C. Following the addition of 0.2 g of a Pd/C catalyst, the apparatus was blanketed with hydrogen by connecting the gas burette. The reaction solution was stirred for ca. 11 h at 95° C.; the hydrogen absorption during this time was 1085 ml. The reaction solution was then cooled to room temperature, the catalyst was filtered off and toluene was stripped off on a rotary evaporator. The residue was distilled over a packed column at a vacuum of 0.4-0.5 mbar. At a transition temperature of 98-100° C., the product 14-dimethyltetradecanolid could be isolated with a purity of >90%.

Example 6

Procedure for the Preparation of
15-Dimethylpentadecanolid—Hydrogenation of the
Double Bond 20 g of 15-dimethylpentadecenolid are introduced as initial charge together with toluene in a 250 ml three-neck flask with a gas burette (1 bar of $H_2$) and heated to 95° C. After adding 0.2 g of a Pd/C catalyst, the apparatus is blanketed with hydrogen by connecting the gas burette. The reaction solution is stirred at 95° C. until no more hydrogen absorption is observed. The reaction solution is then cooled to room temperature, the catalyst is filtered off and toluene is stripped off on a rotary evaporator. The residue is distilled over a packed column at a vacuum of 0.4-0.5 mbar in order to obtain the product 15-dimethylpentadecanolid.

The invention claimed is:

1. A compound of the formulae (I) or (IIa) or a mixture thereof

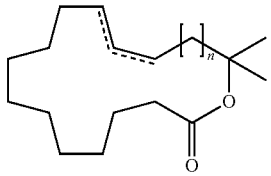

(I)

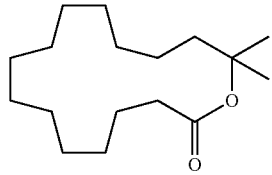

(IIa)

in which n is zero (0) or one (1) and the dashed line is a double bond in 11 or 12 position in cis or trans configuration.

2. The mixture according to claim 1, which furthermore comprises the compound of the formula (IIb)

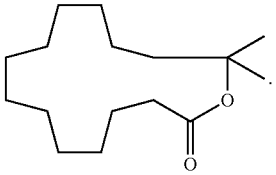

(IIb)

3. The compound of the according to claim 1, wherein the compound of the formula (I) is at least one of the double-bond isomers of the formulae (Ia), (Ib), (Ic) or (Id) or mixtures thereof

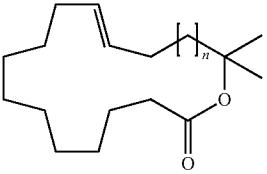

(Ia)

(trans-11)

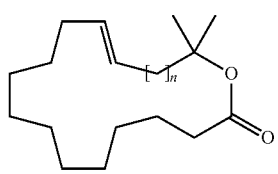

(Ib)

(trans-12)

-continued

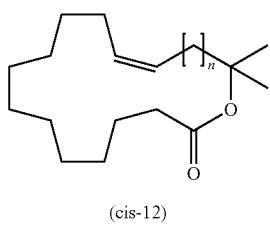
(cis-12)

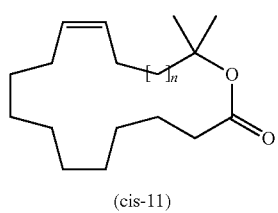
(cis-11)

and n is 0 or 1.

4. A process for the preparation of the compound of the formula (I) according to claim 1 or a compound of the formulae (Ia), (Ib), (Ic) or (Id)

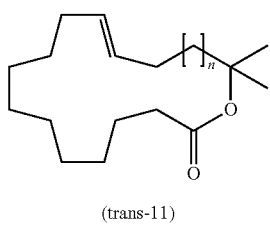
(trans-11)

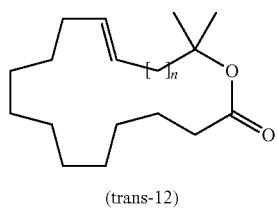
(trans-12)

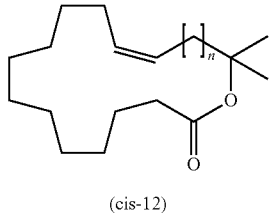
(cis-12)

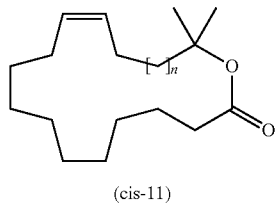
(cis-11)

or a compound of the formula (II)

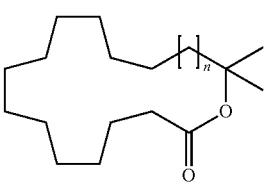
(II)

in which n is zero (0) or one (1)
comprising the reaction steps:
a) alkylating the cyclododecanone of the formula (III)

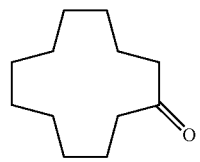
(III)

with a compound of the formula (IVa) or a compound of the formula (IVb)

(IVa)

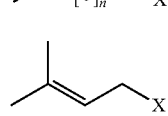
(IVb)

in which, in formula (IVa) and (IVb)
X is a leaving group and
n is zero (0) or one (1),
to give a corresponding compound of the formula (Va) or of the formula (Vb),

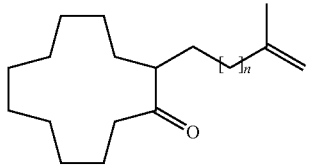
(Va)

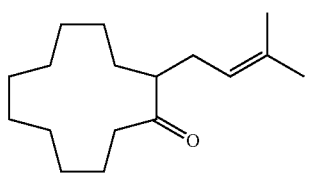
(Vb)

in which, in formula (Va) n is zero (0) or one (1);
b) cyclization of one of the compounds of the formulae (Va) or (Vb) to give a corresponding compound of the formula (VI);

(VI)

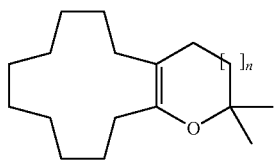

in which, in formula (VI), n is zero (0) or one (1);

c) adding $H_2O_2$ onto the double bond of the compound of the formula (VI) to give a compound of the formula (VII) and subsequent transition metal [TM]—catalyzed fragmentation of the compound of the formula (VII) to give compounds of the formula (I)

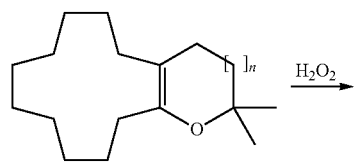

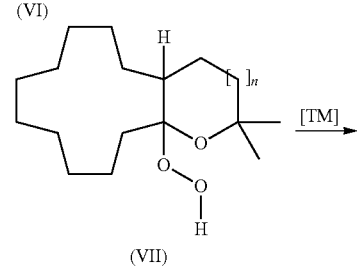

(VII)

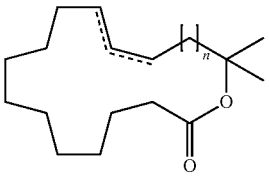

(I)

and optionally d) hydrogenating the compound of the formula (I) to give a compound of the formula (II)

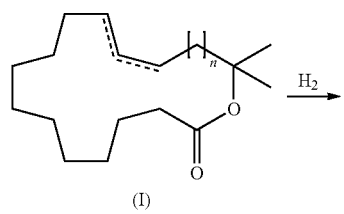

(I)

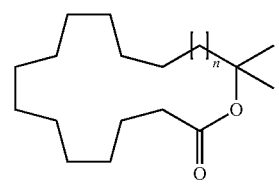

(II)

in which, in the formulae (I), (II) and (VII)
n is zero (0) or one (1) and
the dashed line in formula (I) is an additional double bond in 11 or 12 position in cis or trans configuration.

5. A process for the preparation of the compound of the formula (I) according to claim 1 or a compound of the formulae (Ia), (Ib), (Ic) or (Id)

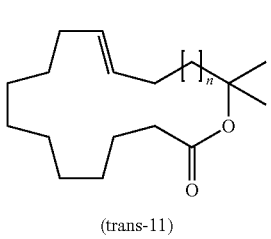

(trans-11)

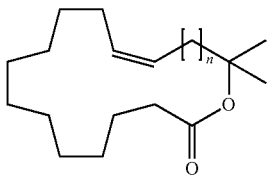

(cis-12)

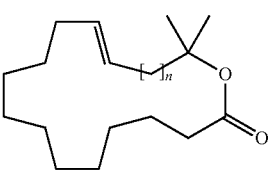

(trans-12)

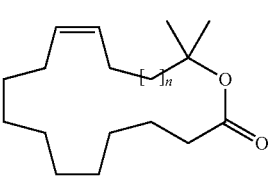

(cis-11)

or a compound of the formula (II)

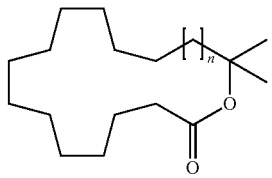

(II)

in which n is zero (0) or one (1)

comprising, as one of the reaction steps, a cyclization of a compound of the formula (Va) or of the formula (Vb), (Va)

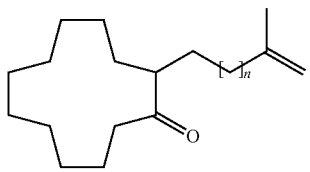

-continued (Vb)
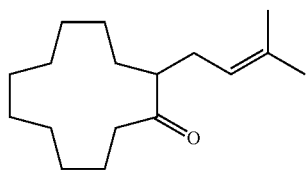

to give a corresponding compound of the formula (VI);

(VI)
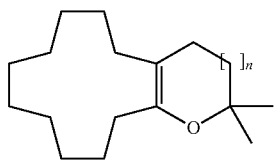

in which, in formulae (Va) and (VI), n is zero (0) or one (1), wherein the cyclization is carried out in the presence of a Brönsted acid or Lewis acid as reactive distillation, where the compound of the formula (VI) formed is separated off from the compound of the formula (IIIa) or of the formula (IIIb) by distillation from the reaction mixture.

6. A fragrance which comprises the compound of the formula (I) according to claim 1, or a compound of the formulae (Ia), (Ib), (Ic) or (Id)

(Ia)
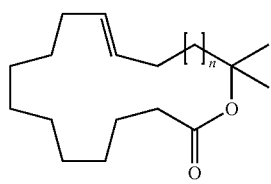
(trans-11)

(Ic)
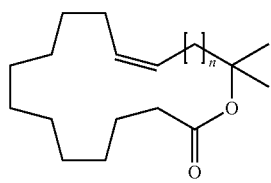
(cis-12)

(Ib)
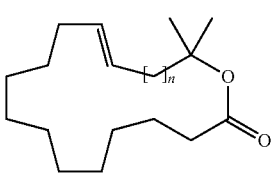
(trans-12)

(Id)
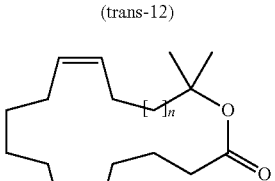
(cis-11)

or a compound of the formula (II)

(II)
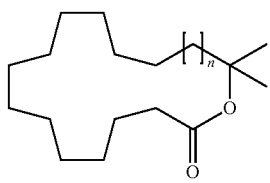

in which n is zero (0) or one (1).

7. A fragrance composition comprising at least one of the compounds of the formula (I) according to claim 1 or the formulae (Ia), (Ib), (Ic), (Id) or of the formula (II)

(Ia)
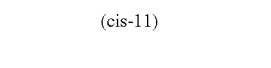
(trans-11)

(Ic)

(cis-12)

(Ib)

(trans-12)

(Id)

(cis-11)

(II)
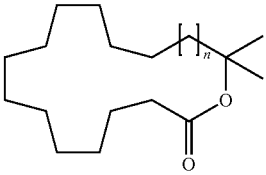

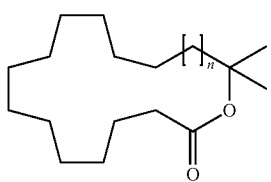
(II)
in which n is zero (0) or one (1)
together with at least one further fragrance.
8. A perfumed or aromatized product or article comprising organoleptically active amounts of at least one of the compounds of the formula (I) according to claim 1 or of the formulae (Ia), (Ib), (Ic) or (Id) or of the formula (II)
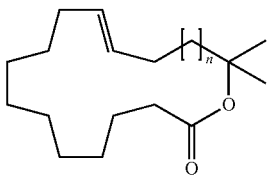
(Ia)
(trans-11)
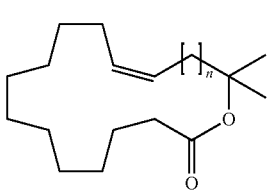
(Ic)
(cis-12)
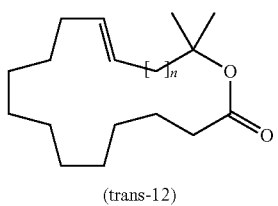
(Ib)
(trans-12)
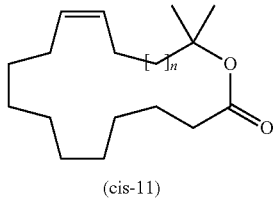
(Id)
(cis-11)
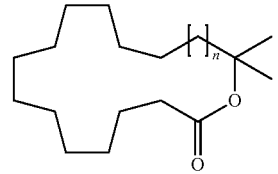
(II)
in which n is zero (0) or one (1).
* * * * *